United States Patent
Salomon et al.

(10) Patent No.: US 11,064,965 B2
(45) Date of Patent: Jul. 20, 2021

(54) NOISE-ROBUST REAL-TIME EXTRACTION OF THE RESPIRATORY MOTION SIGNAL FROM PET LIST-DATA

(71) Applicant: KONINKLIJKE PHILIPS N.V., Eindhoven (NL)

(72) Inventors: Andre Frank Salomon, Aachen (DE); Bin Zhang, Cleveland, OH (US); Andreas Goedicke, Aachen (DE); Patrick Olivier, Solon, OH (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 115 days.

(21) Appl. No.: 16/493,060

(22) PCT Filed: Mar. 26, 2018

(86) PCT No.: PCT/EP2018/057623
§ 371 (c)(1),
(2) Date: Sep. 11, 2019

(87) PCT Pub. No.: WO2018/172566
PCT Pub. Date: Sep. 27, 2018

(65) Prior Publication Data
US 2020/0008770 A1    Jan. 9, 2020

Related U.S. Application Data

(60) Provisional application No. 62/476,062, filed on Mar. 24, 2017.

(51) Int. Cl.
*A61B 6/00* (2006.01)
*A61B 6/03* (2006.01)
*G06T 7/20* (2017.01)

(52) U.S. Cl.
CPC ............ *A61B 6/5264* (2013.01); *A61B 6/032* (2013.01); *A61B 6/037* (2013.01); *A61B 6/5235* (2013.01);
(Continued)

(58) Field of Classification Search
CPC ..... A61B 6/5264; A61B 6/032; A61B 6/5235; A61B 6/037; G06T 7/20; G06T 2207/30004; G06T 2207/10104
See application file for complete search history.

(56) References Cited

U.S. PATENT DOCUMENTS

2008/0273785 A1   11/2008  Kesner
2011/0116695 A1    5/2011  Wollenweber
(Continued)

FOREIGN PATENT DOCUMENTS

WO    2016178115 A1   11/2016

OTHER PUBLICATIONS

Kesner, Al et al, "A new fast and fully automated software based algorithm for extracting respiratory signal from raw PET data and its comparison to other methods", Medical Physics, vol. 37, No. 10, Oct. 2010—Abstract Only.

*Primary Examiner* — Brenda C Bernardi (57) ABSTRACT

A respiratory motion signal generation method operates on emission data (22) of an imaging subject in an imaging field of view (FOV) acquired by a positron emission tomography (PET) or single photon emission computed tomography (SPECT) imaging device (10). An array of regions (32) is defined in the imaging FOV without reference to anatomy of the imaging subject. For each region of the array of regions defined in the imaging FOV, an activity position versus time curve (54) is computed from the emission data acquired by the PET or SPECT imaging device. Frequency-selective filtering of the activity position versus time curves is per-
(Continued)

formed to generate filtered activity position versus time curves. At least one motion signal (66) is generated by combining the filtered activity position versus time curves of at least a selected sub-set of the regions.

18 Claims, 5 Drawing Sheets

(52) U.S. Cl.
CPC ...... *G06T 7/20* (2013.01); *G06T 2207/10104* (2013.01); *G06T 2207/30004* (2013.01)

(56) References Cited

U.S. PATENT DOCUMENTS

| | | |
|---|---|---|
| 2012/0275657 A1 | 11/2012 | Kolthammer |
| 2013/0085375 A1 | 4/2013 | Hamill |
| 2014/0276029 A1 | 9/2014 | Wollenweber |
| 2015/0065854 A1* | 3/2015 | Ahn ................. A61B 6/037 600/411 |
| 2016/0095565 A1 | 4/2016 | Fenchel |

* cited by examiner

NOISE-ROBUST REAL-TIME EXTRACTION OF THE RESPIRATORY MOTION SIGNAL FROM PET LIST-DATA

CROSS-REFERENCE TO PRIOR APPLICATIONS

This application is the U.S. National Phase application under 35 U.S.C. § 371 of International Application No. PCT/EP2018/057623, filed on Mar. 26, 2018, which claims the benefit of U.S. Provisional Patent Application No. 62/476,062, filed on Mar. 24, 2017. These applications are hereby incorporated by reference herein.

FIELD

The following relates generally to the medical imaging arts, emission imaging arts, positron emission tomography (PET) imaging arts, single photon emission computed tomography (SPECT) imaging arts, patient monitoring arts, respiratory monitoring arts, and related arts.

BACKGROUND

In emission imaging, such as positron emission tomography (PET) or single photon emission computed tomography (SPECT), a patient or other imaging subject is administered a radiopharmaceutical designed to preferentially accumulate in a target organ or tissue and that includes a radioactive isotope, e.g. a positron-emitting isotope in PET. The imaging subject is loaded into the imaging device (e.g. a PET scanner for PET imaging, or a gamma camera for SPECT imaging) and emission imaging data are collected and reconstructed, typically using an iterative reconstruction algorithm, to generate a reconstructed image. For improved accuracy, an attenuation map of the imaging subject may be provided, for example computed from a transmission computed tomography (CT) image of the subject, and the attenuation map is used to correct the reconstruction for attenuation of the detected radiation (e.g. 511 keV gamma rays in the case of PET) in the body of the imaging subject.

Depending upon the size of the region of interest, the subject may remain in a single fixed position for the entire emission imaging session; or, if a larger volume is to be imaged than can be captured in a single field-of-view (FOV) of the imaging device then multi-stage imaging may be employed in which the subject support (e.g. couch) moves the patient stepwise through the imaging FOV with a separate image acquired at each step. Continuous patient motion is also a possibility, i.e. the patient may be moved through the FOV in continuous fashion during the imaging data acquisition and the resulting data adjusted for patient position at time of acquisition to generate an image larger than the imaging device FOV.

A known source of image degradation is motion of the subject. One such motion source is respiration. One way to reduce respiration motion artifacts is to process data acquired during a single respiratory phase—for this purpose, end-expiration is often chosen as it is relatively quiescent and of relatively long duration (typically ~30% of the respiratory cycle). The respiration may be monitored using a breathing belt or other dedicated device. However, such a device can be uncomfortable for the patient, and may contribute to scattering and/or absorption of the measured radiation, thereby degrading image quality.

Other approaches, known as "data driven" approaches, attempt to extract the respiration signal from the emission imaging data. Such approaches are effective in the case of an imaging modality such as transmission computed tomography (CT) imaging, in which a strong signal is obtained from which an anatomical feature such as the lung/diaphragm interface may be delineated and monitored for respiratory motion. Data driven approaches are less readily applied to emission imaging. This is due to the low radiopharmaceutical dosage employed in the interest of patient radiological safety, which results in low emission signal strength and consequent low signal-to-noise ratio (SNR). Moreover, emission imaging typically captures functional information, e.g. high metabolism carcinogenic tumors are typically the "bright" features or "hot spots" due to high vasculature in the tumor leading to high concentration of the administered radiopharmaceutical in the tumor.

Kesner, U.S. Pub. No. 2008/0273785 ("Kesner") discloses a data-driven approach for extracting a respiratory signal for retrospective gating of PET images. In this approach, a time series of PET images is generated at 0.5 sec time intervals, and a frequency-filtered activity-versus-time curve is extracted for each voxel of the image. By filtering to limit to respiratory frequency, the activity-versus-time curves are expected to correlate with respiration, and these are combined to generate the respiratory signal. Voxel weighting may be employed, with voxel weights being based on the mean value of the activity-versus-time curve, or based on proximity of the voxel to spatial gradients. Some voxel weights may be set to zero so as to exclude those voxels from contributing to the combined respiratory signal.

The following discloses new and improved apparatuses and methods.

SUMMARY

In one disclosed aspect, an emission imaging data processing device comprises an electronic processor and a non-transitory storage medium storing instructions readable and executable by the electronic processor to perform a respiratory motion signal generation method as follows. A positron emission tomography (PET) or single photon emission computed tomography (SPECT) imaging device is operated to acquire emission data of an imaging subject in an imaging field of view (FOV). For each region of an array of regions defined in the imaging FOV, an activity position versus time curve is computed from the emission data acquired by the PET or SPECT imaging device. At least one respiratory motion signal is generated by combining the activity position versus time curves of at least a sub-set of the regions of the array of regions after frequency-selective filtering of the activity position versus time curves to select content in a respiratory frequency band.

In another disclosed aspect, a motion signal generation method operates on emission data of an imaging subject in an imaging FOV acquired by a PET or SPECT imaging device. The motion signal generation method comprises: defining an array of regions in the imaging FOV without reference to anatomy of the imaging subject; for each region of the array of regions defined in the imaging FOV, computing an activity position versus time curve from the emission data acquired by the PET or SPECT imaging device; performing frequency-selective filtering of the activity position versus time curves to generate filtered activity position versus time curves; and generating at least one motion signal by combining the filtered activity position versus time curves.

In another disclosed aspect, an emission imaging data processing device is disclosed, including a PET or SPECT imaging device, an electronic processor, and a non-transitory storage medium storing instructions readable and executable by the electronic processor to perform a respiratory motion signal generation method. That method includes: operating the PET or SPECT imaging device to acquire emission data of an imaging subject in an imaging FOV; computing activity maps from the emission data for successive time intervals in a region defined in the imaging FOV; computing a transaxial activity position versus time curve from the activity maps, the transaxial activity position comprising a minimum distance of the centroid of the activity map from an axial anatomical axis (z) of the imaging subject; and generating a respiratory motion signal based on at least the transaxial activity position versus time curve.

One advantage resides in generation of a respiratory signal with reduced noise.

Another advantage resides in providing more robust respiratory gating of emission imaging.

Another advantage resides in providing a respiratory signal generated with low time latency so as to be displayed concurrently with emission imaging data collection.

Another advantage resides in providing automated respiratory signal generation from emission data without reference to anatomy of the imaging subject.

Another advantage resides in providing automated respiratory signal generation from emission data which detects whether respiratory motion is present.

Another advantage resides in providing more than one respiratory signal generation from emission data, which enables detection of phase-shift between respiratory motion in e.g. upper abdomen and lower abdomen.

A given embodiment may provide none, one, two, more, or all of the foregoing advantages, and/or may provide other advantages as will become apparent to one of ordinary skill in the art upon reading and understanding the present disclosure.

BRIEF DESCRIPTION OF THE DRAWINGS

The invention may take form in various components and arrangements of components, and in various steps and arrangements of steps. The drawings are only for purposes of illustrating the preferred embodiments and are not to be construed as limiting the invention.

DETAILED DESCRIPTION

Approaches for retrospective respiratory gating, such as that of Kesner discussed previously herein, have certain disadvantages. They entail performing an image reconstruction for each time interval (e.g. 0.5 sec time windows in Kesner) in order to determine the activity at each voxel in each time interval. A trade-off is made between temporal resolution (improved by using a shorter time window) and noise (improved for each reconstructed image by using a longer time window). The image reconstruction is computationally costly, is not conducive to real-time respiratory signal extraction, and cannot leverage time-of-flight localization in an efficient manner.

The noise can in principle be reduced by combining the activity-versus-time curves of all voxels in the imaging field of view (FOV) to generate the respiratory signal. However, most voxels will not have a strong respiratory signal component, and thus may contribute more noise than signal to the combined respiratory signal. Voxel weighting based on the mean value of the activity-versus-time curve, or based on proximity of the voxel to spatial gradients, may be used to preferentially combine voxels with a stronger respiratory cycling component. However, weighting based on the mean value of the activity-versus-time curve can itself be noisy due to noise of that curve; while, weighting based on proximity to spatial gradients requires processing of the reconstructed images to identify regions of large spatial gradients, and even so those gradients may not be associated with a strong respiratory signal component.

Data driven respiratory motion signal generation techniques disclosed herein overcome these and other disadvantages of existing techniques. The approaches disclosed herein are anatomy-agnostic and do not require a priori knowledge of (or post-reconstruction processing identification of) regions of large spatial gradient or other anatomical features of the patient. The disclosed approaches are well-suited to emission imaging as they automatically focus the respiratory signal extraction on so-called "hot spots", i.e. lesion-sized regions of high radioactivity that move with respiratory motion. The disclosed approaches are region-based, rather than voxel-based, and are expected to exhibit improved SNR. The regions may be tailored to the expected lesion size, but are not required to match with extant lesions either in terms of location or size. Still further, the disclosed approaches automatically detect when the imaging FOV is not strongly affected by respiratory motion, in which case respiratory motion correction may be appropriately omitted.

The disclosed respiratory motion signal generation approaches have further advantages. They do not employ computationally costly image reconstruction, but instead employ back-positioning. In general, backpositioning is performed by calculating, for a detected decay event, a most likely decay event location in three-dimensional space. In the case of time-of-flight (TOF) positron emission tomography (PET) imaging, the back-positioning may advantageously leverage TOF localization along a line-of-response (LOR) to provide more accurate back-positioning. In this case, each event is suitably assigned a location probability along the LOR according to a Gaussian distribution model (or other chosen probability distribution), and the backpositioning for that event is where the maximum probability value is found. In the case of non-TOF PET or single photon emission computed tomography (SPECT) imaging, the back-positioning can be performed by, for example, setting the back-position value of each voxel to the count of LORs or SPECT projections that pass through the voxel. In either case, rapid generation of an activity map by back-positioning facilitates performing real-time extraction of a respiratory motion signal if desired. Still further, the disclosed approaches generate an activity position curve for each region thereby providing additional information as compared with a simple voxel activity versus time curve. In some embodiments of the disclosed approaches, both transaxial and transverse motion curves are generated, which can more effectively capture the spatial characteristics of the respiratory motion.

Figure 1:
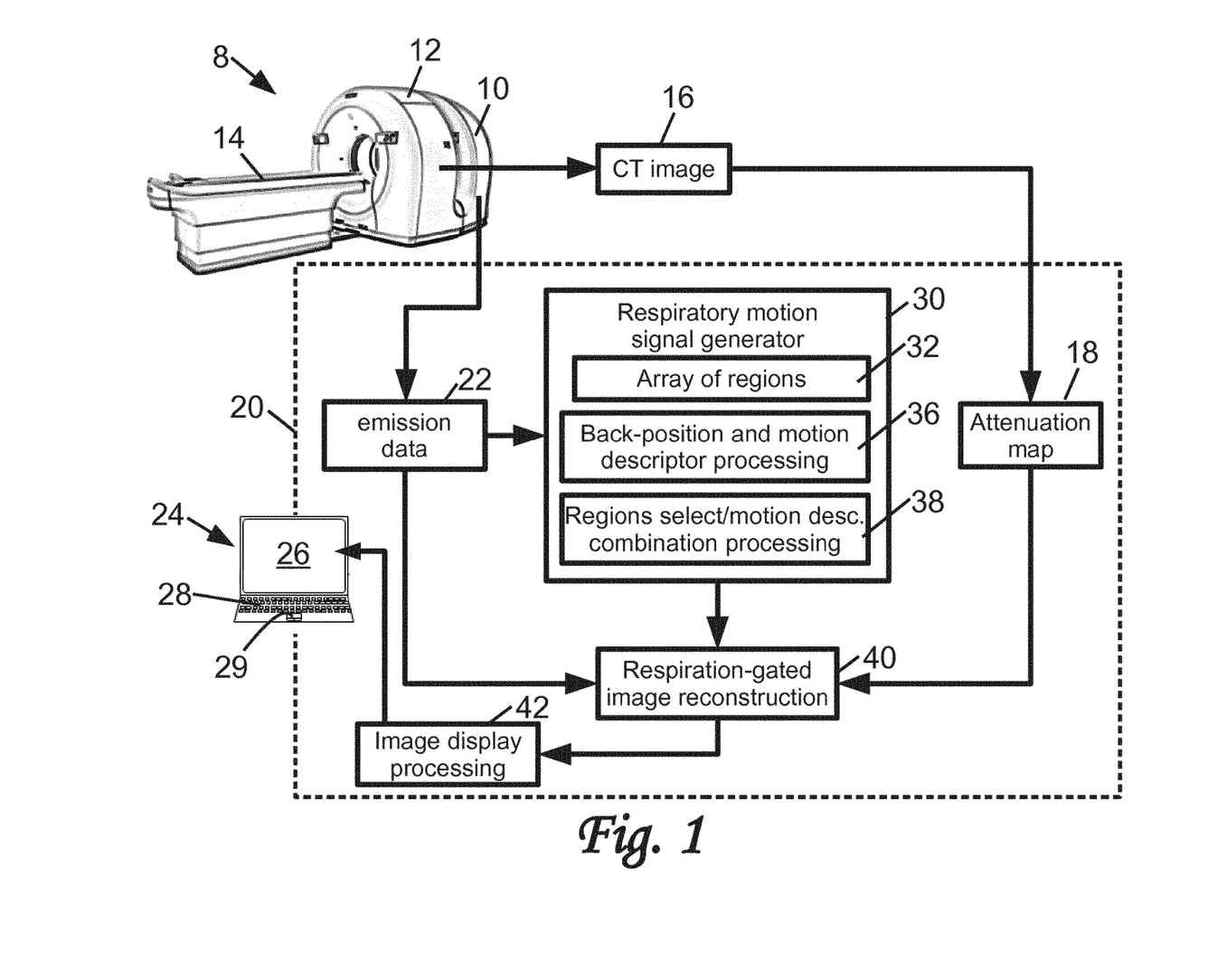
FIG. 1 diagrammatically illustrates an emission imaging device providing imaging and also data driven generation of a respiration motion signal.

With reference to FIG. 1, an illustrative emission imaging system comprises a combined positron emission tomography (PET)/transmission computed tomography (CT) imaging device 8, which includes both a PET imaging gantry or scanner 10 and a CT gantry or scanner 12 mounted with coaxial bores such that a patient may be loaded onto a common patient table 14 and loaded into either the CT gantry 12 for CT imaging or the PET gantry 10 for PET imaging. The PET imaging gantry or scanner 10 has radiation detectors for detecting 511 keV gamma rays, and a line of response (LOR) is defined by two substantially simultaneous gamma ray detections presumed to originate from a single positron-electron annihilation event. In some embodiments, the radiation detectors of the PET gantry are high-speed detectors which are capable of detecting the time difference between the detections of the two 511 keV gamma rays emitted by a single positron-electron annihilation event. This measured time difference enables further time-of-flight (TOF) localization of the positron-electron annihilation event along the LOR. Each LOR is time stamped with the acquisition time (the finite TOF difference is usually on the order of picoseconds, and for LOR time stamping purposes is negligible). The CT gantry 12, if provided, acquires transmission CT images 16 which may, for example, be used to generate an attenuation map 18 by appropriate conversion of the Hounsfield numbers of the CT image 16 to corresponding absorption values at 511 keV (the energy of gamma rays emitted during positron-electron annihilation events). By way of non-limiting illustrative example, the illustrative PET/CT imaging device imaging scanner 8 may be the PET gantry of a Vereos™ Digital PET/CT scanner, available from Koninklijke Philips N.V., Eindhoven, the Netherlands.

The illustrative emission imaging device is a PET imaging device 10 which acquires emission imaging data in the form of time stamped LORs; in other embodiments the emission imaging device may be a gamma camera which acquires emission imaging data in the form of single photon emission computed tomography (SPECT) projection data. In SPECT imaging, each projection is defined by a single radiation photon or particle detection event, and is again time stamped. As is known in the art, the projections in SPECT imaging are spatially limited to a plane or (more commonly) to a narrow-angle cone or line, through the use of a collimator made of radiation-absorbing high atomic weight (high-Z) material, such as lead or a lead compound, which is mounted on the radiation detector head. As with PET imaging, the optional CT gantry 12 can generate a CT image 16 that is converted to an attenuation map 18 for performing attenuation correction during the SPECT reconstruction.

As diagrammatically shown in FIG. 1, an electronic processor 20 processes emission data 22 acquired by the PET imaging gantry or scanner 10 (comprising LORs in the illustrative PET imaging embodiment, or comprising projections acquired by a gamma camera in an alternative SPECT imaging embodiment) to generate a respiratory motion signal and to generate a reconstructed image. The electronic processor 20 may, for example, be embodied as a computer 24 (e.g. a desktop computer, network-based server computer, a dedicated imaging device control computer, various combinations thereof, or so forth) that executes instructions read from one or more non-transitory storage media (e.g. one or more hard drives, optical disks, solid state drives or other electronic digital storage devices, various combinations thereof, or so forth) that stores the instructions. The computer 24 typically includes or has operative access to at least one display 26 (e.g. an LCD display, plasma display, or so forth) for displaying reconstructed images, and optionally also including one or more user input devices such as an illustrative keyboard 28, an illustrative trackpad 29 (or mouse, trackball, touch-sensitive overlay of the display 26, or other pointing device), or so forth.

The emission imaging data 22 is acquired over a relatively extended period, that is, over a time interval encompassing many breaths performed by the imaging subject, in order to provide enough emission imaging data to achieve an acceptable signal to noise ratio (SNR). As diagrammatically indicated in FIG. 1, the electronic processor 20 is programmed by instructions stored on a non-transitory storage medium to perform a respiratory motion signal generation process 30 which operates on the emission imaging data 22. The illustrative respiratory motion signal generation process 30 operates on a pre-defined set of region definitions 32. For example, the image field of view (FOV) of the PET imaging gantry or scanner 10 may be divided into regions comprising a spatial array of spherical (or cylindrical, or otherwise-shaped) regions which preferably overlap so as to cover substantially the entire imaging FOV. Time intervals are also defined, typically as time bins of a selected duration, e.g. one second per time interval in one illustrative example. The time intervals may optionally overlap temporally. For each region of the array of regions 32 and each time interval, back-position and motion descriptor processing 36 are performed to generate a position descriptor (or a plurality of position descriptors, in alternative embodiments). For example, a position descriptor may comprise the centroid of the activity in the region along the z-direction (transaxial position). Additionally or alternatively, a position descriptor may comprise the radial distance of the centroid of the activity in the region from a center of the region in the x-y plane (transverse position; that is, the descriptor is the minimum distance of the centroid of the activity map from the axial anatomical axis, z, of the imaging subject). Region selection and motion descriptor combination processing 38 then combines the position descriptors of those regions having strongest indication of respiratory motion to generate the final respiratory motion signal.

The electronic processor 20 is further programmed by instructions stored on (the same or a different) non-transitory storage medium to perform a respiration-gated image reconstruction process 40 that operates on the emission data 22, the respiratory motion as estimated by the respiratory motion signal generation process 30, and optionally further based on the attenuation map 18, to perform attenuation correction of the reconstructed PET image. The illustrative respiration-gated image reconstruction process 40 operates to reconstruct a sub-set of the emission data 22 corresponding to a selected respiratory phase (typically end-exhalation, as this phase is quiescent and of long duration) to generate a reconstructed image with reduced blurring due to respiratory motion. For example, the image reconstruction 40 may employ an iterative image reconstruction technique such as maximum likelihood-expectation maximization (MLEM), ordered-subset expectation-maximization (OSEM), or so forth, and may optionally include regularization using an edge-preserving noise-suppressing prior, scatter correction, or other known techniques for enhancing image quality.

The illustrative electronic processor 20 is further programmed by instructions stored on (the same or a different) non-transitory storage medium to perform image display processing 42 to generate a visualization of the reconstructed image, such as a single two-dimensional (2D) slice image, a 2D maximum intensity projection (MIP), a three-dimensional (3D) rendering of the volumetric reconstructed image, or so forth, which may be displayed on the at least on display 26, and/or stored to a Picture Archiving and Communication System (PACS), and/or printed by a printing device, and/or otherwise utilized.

Figure 2:
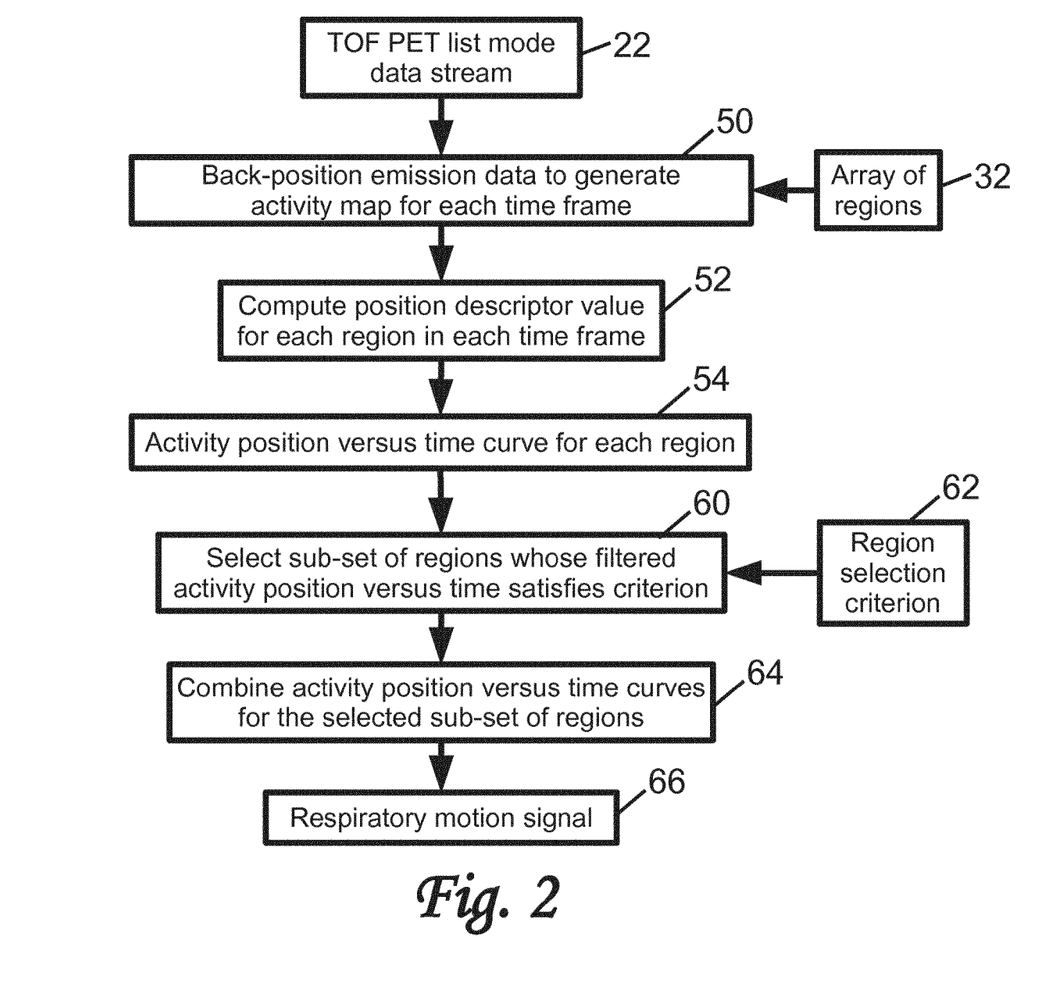
FIG. 2 diagrammatically illustrates data driven generation of a respiration motion signal as suitably performed by the device of FIG. 1.

With continuing reference to FIG. 1 and with further reference to FIG. 2, an illustrative embodiment of the respiratory motion signal generation process 30 is described. In this illustrative example, the emission data 22 comprise a time of flight (TOF) positron emission tomography (PET) list mode data stream. Each emission datum comprises a line of response (LOR) defined between two nearly simultaneous (i.e. within a defined coincidence time window) 511 keV gamma ray detections, with TOF localization along the LOR based on the time difference (or lack thereof) between the two 511 keV gamma ray detection events. In an operation 50, the emission data acquired over each time interval are back-positioned to generate an activity map for each time interval and for each region of the array of regions 32. The operation 50 can be carried out by performing the backpositioning for all emission data in the time window to generate an activity map for the entire imaging FOV and then spatially segmenting that activity map to generate activity maps for the individual regions of the array of regions 32. Alternatively, the operation 50 can be carried out by performing backpositioning separately for each region of the array of regions 32. In the illustrative example of TOF PET emission data, the activity map of the region is generated by back-positioning each LOR to its maximum TOF likelihood position along the LOR. (This differs from image reconstruction which makes use of the TOF probability distribution along the LOR to provide more accurate image reconstruction compared with the activity map generated in operation 50 by backpositioning).

In an operation 52, for each region of the array of regions 32 and for each time interval, a value of a position descriptor is computed. For example, a position descriptor may comprise the centroid of the activity in the region along the z-direction (transaxial position). Additionally or alternatively, a position descriptor may comprise the radial distance of the centroid of the activity in the region from a center of the region in the x-y plane (transverse position). The result of the operation 52 is an activity position versus time curve 54 for each region of the array of regions 32.

In an operation 60, a sub-set of regions are selected from the array of regions 32 based on whether the region's activity position versus time curve satisfies a region selection criterion 62, such as the fraction of energy in a respiratory frequency band (e.g., between 0.05 Hz and 0.50 Hz in one illustrative example, corresponding to a range of 2-20 seconds/breath) being greater than some threshold. It is contemplated to employ an adjusted respiratory frequency band for special cases, e.g. infant imaging subjects. Typically, it is expected that the operation 60 will select a relatively small number of the regions of the array of regions 32, e.g. perhaps 10-20 regions or fewer may be selected. These selected regions are expected to be regions that contain at least a portion of a hot spot over at least a portion of the breathing cycle, with the hot spot being positioned in a lung, thoracic diaphragm, or other anatomical feature that moves strongly with respiration. The hot spot may, by way of non-limiting illustrative example, be a tumor lesion, or a myocardium muscle, liver edge or other anatomical feature that exhibits a high level of activity. Advantageously, although the hot spots may correlate with anatomy, the operation 60 does not rely upon any a priori knowledge of the anatomy—rather, the optimal sub-set of regions is selected in the operation 60 in empirical fashion, based on the criterion 62.

In an operation 64 the activity position versus time curves of the regions selected in the operation 60 are combined to generate a respiratory motion signal 66. In one approach, the operation 64 includes performing frequency-selective filtering of the activity position versus time curves to select content in the respiratory frequency band (e.g. using a bandpass filter with a pass band of 0.05-0.50 Hz in some embodiments). A correlation is computed of each filtered activity position versus time curve with a reference respiratory motion signal. The reference respiratory motion curve may be the filtered activity position versus time curve of the region that best satisfies the region selection criterion 62, e.g. the curve having the greatest fraction of its energy in the respiratory frequency band in accord with one illustrative criterion. The filtered activity position versus time curve is then added to, or subtracted from, the respiratory motion signal, where the adding or subtracting operation is chosen based on the sign of the correlation.

Figure 3:
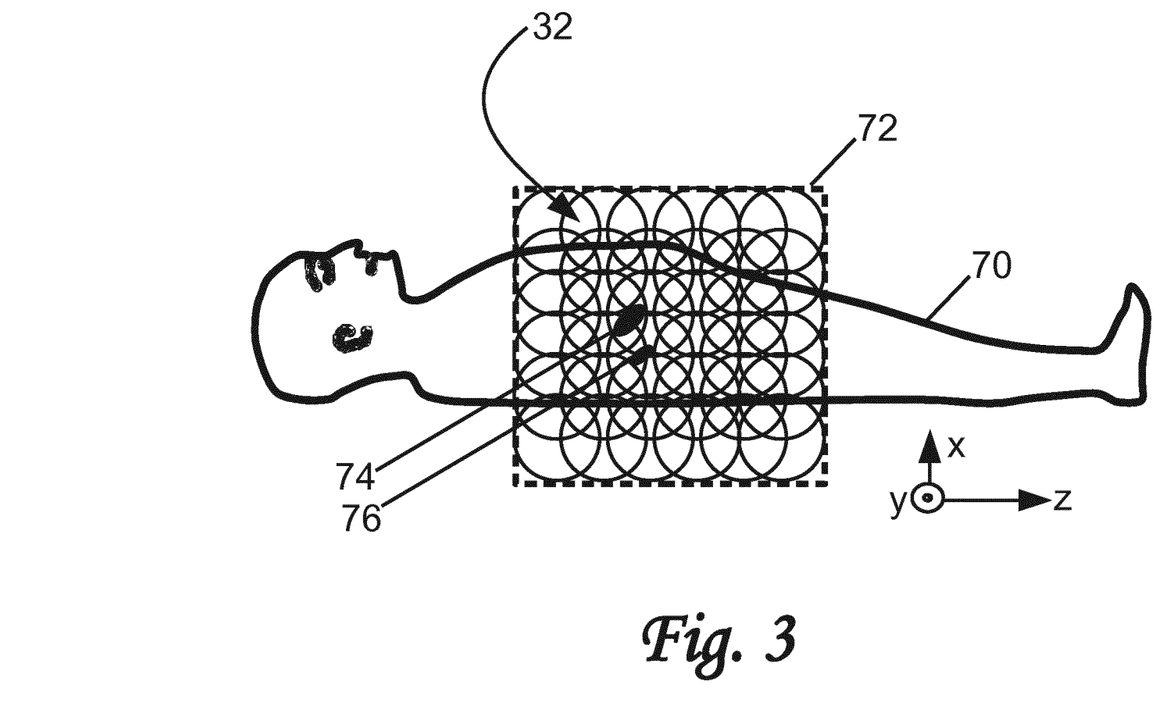
FIGS. 3-6 diagrammatically show aspects of the data driven method of generation of the respiration motion signal shown in FIG. 2.
Figure 4:
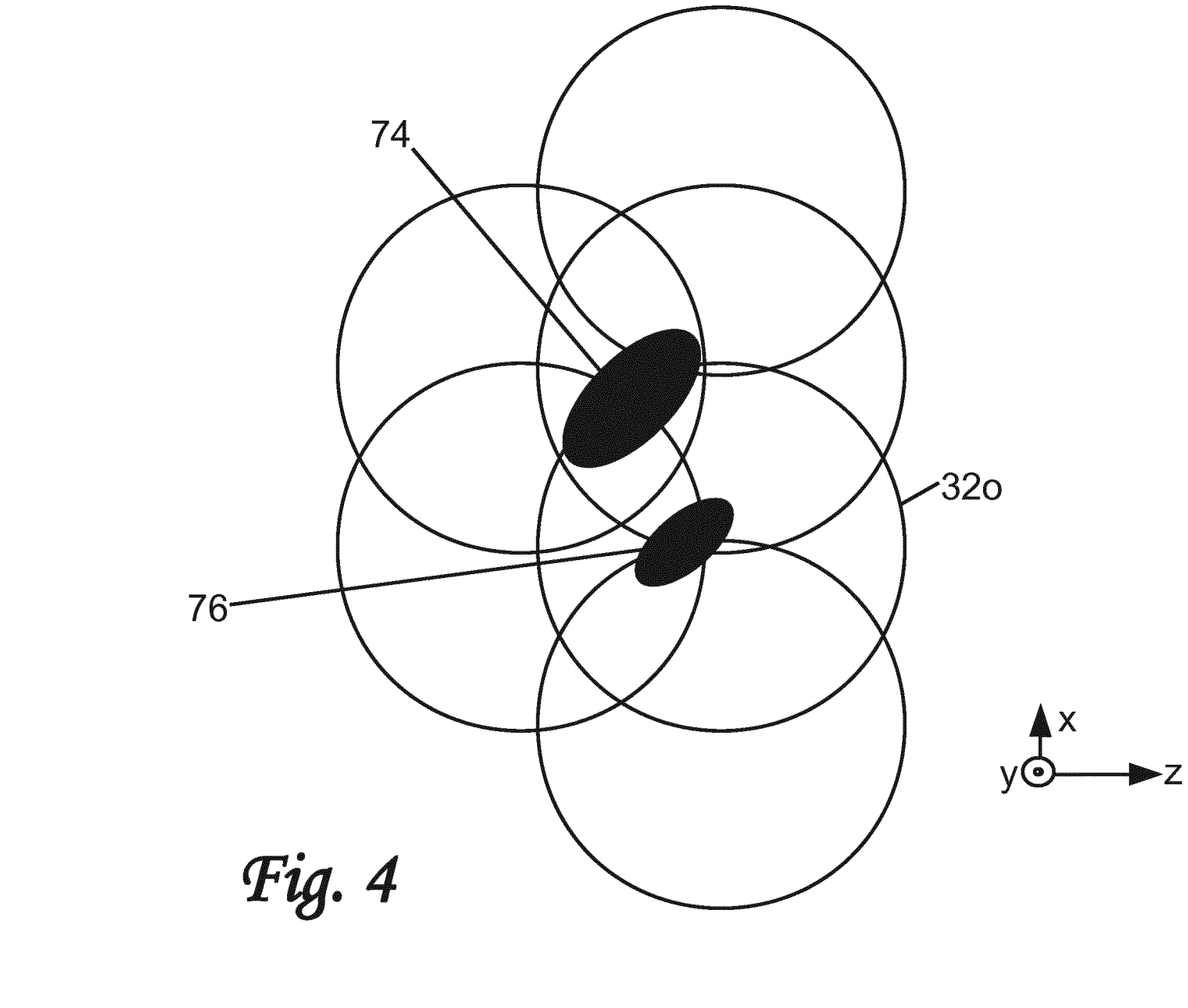
Figure 5:
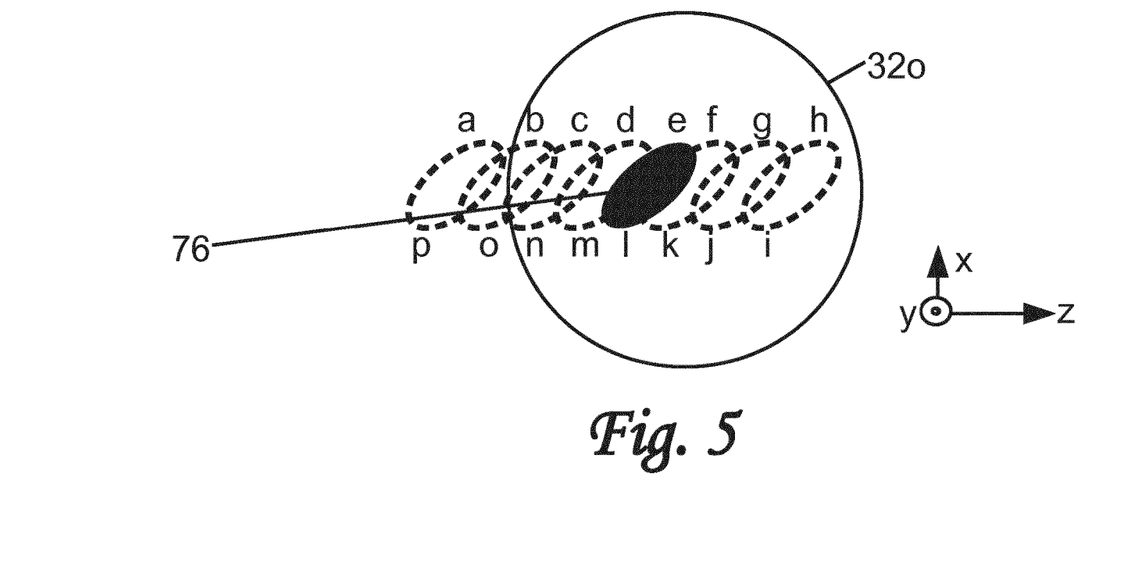
Figure 6:
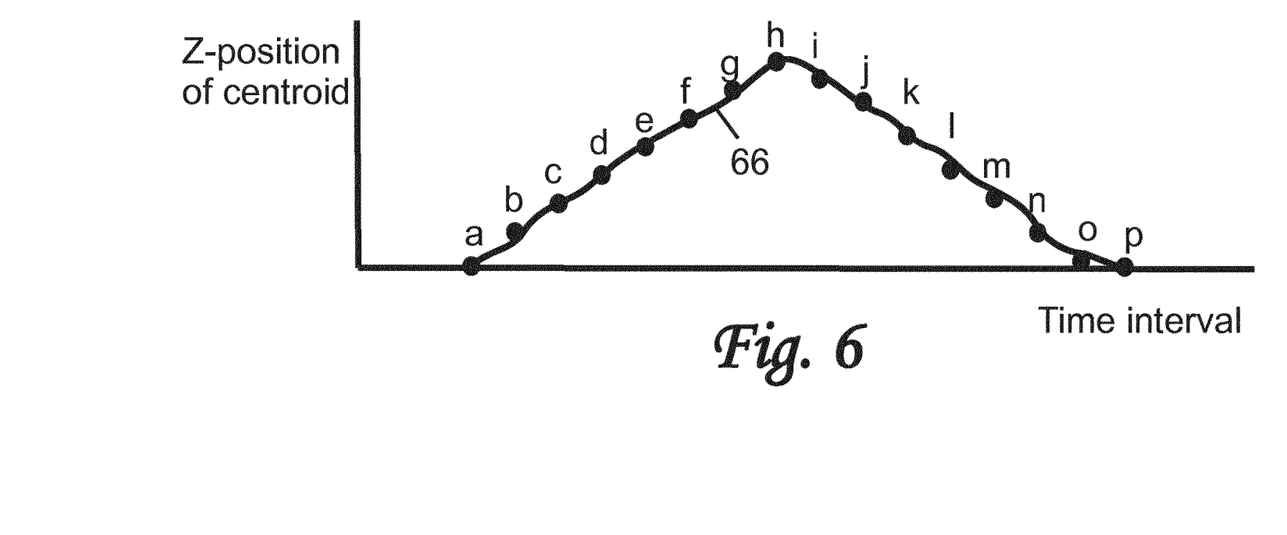

With reference to FIGS. 3-6, the use of the array of regions 32 is further described by way of illustration. FIG. 3 depicts an imaging subject 70 imaged in an imaging FOV 72, which is a volume. The array of regions 32 is defined in the imaging FOV 72. The illustrative regions of the illustrative array of regions 32 are spherical regions which overlap so as to substantially fill the imaging FOV 72, as shown in FIG. 3. Also indicated in FIG. 3 are two hot spots 74, 76, which may for example be malignant tumors of high metabolic activity that preferentially absorb the radiopharmaceutical and hence appear as regions of high activity in the PET imaging. FIG. 4 illustrates an enlarged view in the vicinity of the two hot spots 74, 76, with one particular region 32o labeled which contains the hot spot 76. FIG. 5 illustrates movement of the hot spot 76 with respiration, with successive time intervals labeled "a", "b", "c", . . . , "n", "o", and "p". FIG. 6 shows a plot of the centroid of the activity for each time interval "a", "b", "c", . . . , "n", "o", and "p", and the resulting activity position versus time curve 66 plotted. The drawings are diagrammatic representations: in some expected actual implementations, the typical highest motion amplitudes are anticipated to be on the order of 2-3 cm or less—so in practice the trajectory of motion affected features is usually contained by at least a single spherical region. In FIG. 5, given a typical region's diameter of 10 cm, a large motion trajectory including e.g. all positions a, b, . . . , h as illustrated in FIG. 6 may therefore be an unusual case, and a more typical motion trajectory may include only a,b,c,d, or only e,f,g,h.

The disclosed approaches for generating a respiratory signal are both fast and noise-robust, and provide enhanced accuracy both in the derived amplitude and respiratory cycle-gating signal extraction. In the disclosed approaches, an array 32 of many overlapping regions (e.g. 400-500 spherical regions) are considered and their activity position (e.g. centroid) tracked. By this, simultaneous motion components in opposite direction do not cancel out each other by global averaging, and motion information of small tumors is less masked by noise contained in the emission data outside the particular region. For all local respiratory motion curves (one for each of the aforementioned regions) an individual likelihood is computed whether the region contains significant respiratory motion information (e.g. via operation 60 of FIG. 2). In a suitable approach, this employs a selection criterion 62 that is based on the fraction of respiration-characteristic frequencies in each signal curve. Only high likelihood signal components (i.e. regions) are used for calculating a global motion signal 66. By this, most of the detected noise is excluded from the global respiratory signal estimate. In order to decide, whether the activity position versus time curve of a region should be added or subtracted in the signal combination process 64, the cross-correlation between the (intermediate) global curve estimate and each new region curve is suitably calculated. Using the resulting sign information, motions in opposite spatial directions are not cancelled out. Instead, the quality of the final respiratory signal curve 66 is improved.

In addition to the average axial (z-direction) position of the list-mode events, also transaxial motion information is optionally included and by this the motion signal-to-noise ratio is further increased in the processed data. This is achieved via a patient motion modeling using two main components of a cylindrical coordinate system, the radial component (in the transaxial plane) and z-component (in axial direction).

Advantageously, the disclosed respiratory motion signal generation method can be performed in real-time after an initial acquisition phase where the most motion-affected regions have been identified. In FIG. 2, this corresponds to (after the initial selection of regions via operation 60), repeating only the activity position versus time curve updating for those selected regions (corresponding to repeating operations 50, 52 performed only for the selected regions after the initial time intervals) and performing the combining operation 64 only for the selected regions. Said another way, the selection 60 of the sub-set of the regions of the array of regions 32 is performed for initial successive time intervals. After the selection of the sub-set of regions of the array of regions, the computing of the activity position versus time curve 54 and the generating of the respiratory motion signal 66 is performed using only the selected sub-set of regions of the array of regions for subsequent successive time intervals that follow the initial successive time intervals. Such processing can be done in real-time, given sufficient processing power. Optionally, the region selection operation 60 may be repeated occasionally, e.g. each 30 seconds updates of the region likelihoods.

Accuracy of the activity position versus time curve 54 for each region depends in part on how accurately the activity maps generated by the backpositioning operation 50 reflect the true activity distribution. As previously mentioned, the backpositioning operation 50 for TOF PET may utilize the TOF localization information along the LOR. Advantageously, this TOF localization has been trending toward higher spatial resolution (i.e. tighter spatial localization) as successive generations of TOF PET detectors with improved temporal resolution are developed. Accordingly, the disclosed approach should exhibit increasing accuracy with continued improvements in TOF localization resolution.

In the following, some further examples of illustrative embodiments are described. The array of regions 32 suitably includes a number of overlapping, e.g., spherical regions in the imaging FOV, as shown in FIG. 3. For each time interval t with time width T, one or more average activity position descriptors of corresponding TOF events are calculated for each region (optionally during the PET emission data acquisition, or alternatively retrospectively after the acquisition is completed). As illustrative examples, two different activity position descriptors d are used in PET, based on cylindrical coordinates: (i) the local z-axis position representing craniocaudal motion, and (ii) the radial distance from z-axis, containing anteroposterior and mediolateral motion components. A frequency analysis is performed for the resulting activity position versus time curves $s_{r,d}(t)$ of each region r and each descriptor d. The analysis provides the signal energy fraction within a pre-defined respiratory frequency band, symbolically represented here using operator BP (e.g., between ½ Hz and 1/18 Hz, i.e. between 0.05-0.50 Hz), to extract the fraction of energy in the respiratory frequency band:

$$S_{r,d} = \frac{\sum_{\forall t}(BP(s_{r,d}(t)))^2}{\sum_{\forall t}(s_{r,d}(t))^2} \quad (1)$$

where BP( . . . ) is an operator which extracts the component in the respiratory frequency band (e.g. 0.05-0.50 Hz in some embodiments). $S_{r,d}$ is referred to as the fraction of energy in the respiratory frequency band, and can be considered as likelihood that a respiratory motion affected feature is at least partially located inside region r. After normalization using:

$$\overline{s(t)} = \frac{s(t)}{\sqrt{E(s(t))}} \quad (2)$$

where E(s(t)) is the signal energy given by:

$$E(s(t)) = \frac{\sum_{\forall t}(s(t))^2}{L} \quad (3)$$

where L is the discrete signal length with a sampling rate of r=1/T, all resulting respiratory signal curves $\overline{BP\{s_{r,d}(t)\}}$ are sorted using corresponding $S_{r,d}$, and the highest fraction signal curves are combined in order to reduce noise artifacts. In this illustrative example, the region selection criterion 62 which is used is:

$$S_{r,d} \geq \alpha_{thres} \cdot \max_{r,d}\{S_{r,d}\} \quad (4)$$

with, e.g., $\alpha_{thres}$=0.9 in some illustrative embodiments.

For combining the selected signal curves (FIG. 2 operation 64), the global signal curve is first initialized with the highest fraction curve. Subsequently, all remaining selected signal curves are added or subtracted depending on correlation coefficient c, with:

$$c(s_1(t), s_2(t)) = \sum_{\forall t} s_1(t) \cdot s_2(t) \quad (5)$$

according to:

$$s_{global} \rightarrow s_{global} + \text{sign}(c(s_{global}, s_{r,d})) \cdot s_{r,d} \quad (6)$$

for all r and d satisfying Equation (4).

Finally, the resulting global signal curve $s_{global}$ is normalized according to Equation (2) in order to make it easy comparable to, e.g., a measured reference signal. Note, that $s_{global}$ does not contain information about the spatial amplitude or the motion's trajectory, but it can be used for gating of the PET list-mode data and subsequent motion compensated PET imaging.

For real-time applications in which the respiratory motion signal is generated during acquisition of the emission data, if insufficient computational power is available to perform signal processing and signal combining algorithms for each individual time frame (e.g. 0.5 s), then $S_{r,d}$ can be computed and correlation signs are used in Equation (6) for each region after an initial acquisition period (e.g. 30 s). Then, once the fractions and signs of correlations are initially known, the combination of single signals can be reduced to a simple summation according to Equation (6). The fractions and correlation signs can be updated from time to time in order to iteratively increase signal estimation accuracy.

With returning reference to FIG. 2, the operation 60 selects those regions of the array of regions 32 exhibiting strong respiratory motion. However, in some situations there may be no strong respiratory motion. For example, consider a "whole body" scan in which the patient is moved stepwise to scan from head to toe. Scans with the patient positioned with the torso in the imaging FOV can be expected to exhibit strong respiratory motion. By contrast, scans with the patient' head in the imaging FOV, or with the patient's lower legs in the imaging FOV, are likely to exhibit negligible respiratory motion. In such cases, the number of regions selected in the operation 60 may be small, or even zero. This enables automated detection of situations in which no respiratory motion gating is needed. For example, the respiratory motion signal generator may optionally output a zero value for the respiratory motion signal 66 if the selected sub-set of regions of the array of regions includes less than a threshold number of regions satisfying the region selection criterion 62. Referring back to FIG. 1, the respiration-gated image reconstruction 40 may then omit respiratory gating and instead reconstruct all the emission data in cases where the respiratory motion signal is identically equal to zero.

In the illustrative embodiments, the region selection/ motion descriptor combination processing 38 (e.g., illustrative operations 60, 64 of FIG. 2) operate to produce a singular respiratory motion signal 66. However, in other contemplated embodiments this processing may produce two (or more) respiratory motion signals for different portions of the imaging FOV. For example, a phase-shift in the physical respiratory motion signal may be present between respiratory motion in the upper abdomen versus the lower abdomen. Various approaches can be employed. In one approach, an a priori known anatomical compartmentalization of the imaging FOV may be employed, and the disclosed processing (e.g. that of FIG. 2) applied separately to each different compartment (i.e. portion) of the imaging FOV. In another contemplated approach, the activity position versus time curves 54 may be empirically analyzed to identify two or more contiguous regions of the imaging FOV whose regions exhibit different phase offsets of their activity position versus time curves. One way to implement this, employing the framework of Equations (1)-(6), is to use the correlation $c(s_{global}, s_{r,d})$ to assign a phase to each activity position versus time curve, which can be used together with the spatial layout of the regions of the array of regions 32 to identify contiguous portions of the imaging FOV having approximately the same phase. In this approach, the output may include two different respiratory motion signals, e.g. one for the upper abdomen and another for the lower abdomen.

The illustrative embodiments generate a respiratory motion signal. However, analogous processing may additionally or alternatively be performed to generate a cardiac motion signal. To do so, the time interval is reduced to a smaller value appropriate for the faster cardiac cycling, e.g. 0.5/(5 Hz)=0.1 sec in one non-limiting example, and the respiratory frequency band is suitably replaced by a cardiac frequency band encompassing a credible range of cardiac heart rates, e.g. 0.6 Hz to 5.0 Hz in one illustrative example.

The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

The invention claimed is:

1. An emission imaging data processing device comprising:
   an electronic processor; and
   a non-transitory storage medium storing instructions readable and executable by the electronic processor to perform a respiratory motion signal generation method including:
   operating a positron emission tomography (PET) or single photon emission computed tomography (SPECT) imaging device to acquire emission data of an imaging subject in an imaging field of view (FOV);
   for each region of an array of regions defined in the imaging FOV, computing an activity position versus time curve from the emission data acquired by the PET or SPECT imaging device; and
   generating at least one respiratory motion signal by combining the activity position versus time curves of at least a sub-set of the regions of the array of regions after frequency-selective filtering of the activity position versus time curves to select content in a respiratory frequency band;
   wherein the computing of the activity position versus time curve from the emission data acquired by the PET or SPECT imaging device includes:
   generating an activity map of the region for successive time intervals from the emission data acquired by the PET or SPECT imaging device; and
   computing values of a statistical activity position descriptor for the activity maps of the region for the successive time intervals; and
   wherein the statistical activity position descriptor includes a position of the centroid of the activity map along a transverse direction parallel with an axial anatomical axis (z) of the imaging subject, and/or a minimum distance of the centroid of the activity map from an axial anatomical axis (z) of the imaging subject.

2. The emission imaging data processing device of claim 1 wherein the respiratory motion signal generation method further includes:
   selecting a sub-set of the regions of the array of regions for which the activity position versus time curve includes content in the respiratory frequency band satisfying a region selection criterion;
   wherein the at least one respiratory motion signal is generated by combining the activity position versus time curves of only the selected sub-set of regions of the array of regions after frequency-selective filtering of the activity position versus time curves to select content in the respiratory frequency band.

3. The emission imaging data processing device of claim 2 wherein:

the selection of the sub-set of the regions of the array of regions is performed for initial successive time intervals; and after the selection of the sub-set of regions of the array of regions, the computing of the activity position versus time curve and the generating of the at least one respiratory motion signal is performed using only the selected sub-set of regions of the array of regions for subsequent successive time intervals that follow the initial successive time intervals.

4. The emission imaging data processing device of claim 2 wherein the respiratory motion signal generation method further includes:

outputting a zero value for the respiratory motion signal if the selected sub-set of regions of the array of regions includes less than a threshold number of regions satisfying the region selection criterion.

5. The emission imaging data processing device of claim 1 wherein the computing of the activity position versus time curve and the generating of the at least one respiratory motion signal are performed concurrently with the operating of the PET or SPECT imaging device to acquire emission data of the imaging subject in the imaging FOV, and the respiratory motion signal generation method further includes:

operating a display to display the respiratory motion signal as a function of time during the operation of the PET or SPECT imaging device.

6. The emission imaging data processing device of claim 1 wherein the respiratory motion signal generation method further includes:

defining the array of regions in the imaging FOV without reference to anatomy of the imaging subject.

7. The emission imaging data processing device of claim 1 wherein the respiratory motion signal generation method further includes:

defining the array of regions in the imaging FOV with overlapping of the regions.

8. The emission imaging data processing device of claim 1 wherein:

the operating comprises operating a time-of-flight (TOF) PET imaging device to acquire emission data comprising lines of response (LORs) with TOF localization along the LORs; and the generating of the activity map of the region for successive time intervals from the emission data comprises back-positioning each LOR to its maximum TOF likelihood position along the LOR.

9. The emission imaging data processing device of claim 1 wherein the generating of the at least one respiratory motion signal-includes:

frequency-selective filtering the activity position versus time curves to select content in the respiratory frequency band;

computing a correlation of each filtered activity position versus time curve with a reference respiratory motion signal; and adding or subtracting each filtered activity position versus time curve to the respiratory motion signal wherein the adding or subtracting is chosen based on a sign of the correlation.

10. The emission imaging data processing device of claim 9 wherein the generating of the at least one respiratory motion signal includes:

frequency-selective filtering the activity position versus time curves to select content in the respiratory frequency band;

computing a correlation of each filtered activity position versus time curve with a reference respiratory motion signal;

dividing the imaging FOV into two or more portions based on the computed correlations; and for each portion of the imaging FOV, combining the filtered activity position versus time curves for regions in that portion of the imaging FOV to generate a respiratory motion signal for that portion of the imaging FOV.

11. A motion signal generation method operating on emission data of an imaging subject in an imaging field of view (FOV) acquired by a positron emission tomography (PET) or single photon emission computed tomography (SPECT) imaging device, the motion signal generation method comprising:

defining an array of regions in the imaging FOV without reference to anatomy of the imaging subject;

for each region of the array of regions defined in the imaging FOV, computing an activity position versus time curve from the emission data acquired by the PET or SPECT imaging device;

performing frequency-selective filtering of the activity position versus time curves to generate filtered activity position versus time curves; and generating at least one motion signal by combining the filtered activity position versus time curves of at least a sub-set of the regions of the array of regions to select content in a respiratory frequency band;

wherein the computing of the activity position versus time curve from the emission data acquired by the PET or SPECT imaging device includes:

generating an activity map of the region for successive time intervals from the emission data acquired by the PET or SPECT imaging device; and computing values of a statistical activity position descriptor for the activity maps of the region for the successive time intervals; and wherein the statistical activity position descriptor includes a position of the centroid of the activity map along a transverse direction parallel with an axial anatomical axis (z) of the imaging subject, and/or a minimum distance of the centroid of the activity map from an axial anatomical axis (z) of the imaging subject.

12. The motion signal generation method of claim 11 further comprising:

selecting a sub-set of the regions of the array of regions for which the activity position versus time curve includes content in a frequency band satisfying a region selection criterion;

wherein the at least one motion signal is generated by combining the filtered activity position versus time curves of only the selected sub-set of regions of the array of regions.

13. The motion signal generation method of claim 12 wherein the array of regions in the imaging FOV is defined with overlapping of the regions.

14. The motion signal generation method of claim 11 wherein the emission data of the imaging subject in the imaging FOV is acquired by a PET imaging device with TOF localization, and the generating of the activity map of the region for successive time intervals from the emission data comprises back-positioning each line of response (LOR) of the emission data to its maximum TOF likelihood position along the LOR.

15. The motion signal generation method of claim 11 wherein the generating of the at least one motion signal includes:

computing a correlation of each filtered activity position versus time curve with a reference motion signal; and     adding or subtracting each filtered position versus time curve to the respiratory motion signal wherein the adding or subtracting is chosen based on a sign of the correlation.

16. The motion signal generation method of claim 11 wherein:

performing frequency-selective filtering of the activity position versus time curves to generate filtered activity position versus time curves comprises bandpass filtering the activity position versus time curves using a bandpass filter having a respiratory frequency passband; and     the generating comprises generating the at least one motion signal as a respiratory motion signal by combining the bandpass filtered activity position versus time curves.

17. An emission imaging data processing device comprising:

a positron emission tomography (PET) or single photon emission computed tomography (SPECT) imaging device;

an electronic processor; and a non-transitory storage medium storing instructions readable and executable by the electronic processor to perform a respiratory motion signal generation method including:

operating the PET or SPECT imaging device to acquire emission data of an imaging subject in an imaging field of view (FOV);

computing activity maps from the emission data for successive time intervals in a region defined in the imaging FOV;

computing a transaxial activity position versus time curve from the activity maps, the transaxial activity position comprising a minimum distance of the centroid of the activity map from an axial anatomical axis (z) of the imaging subject; and         generating a respiratory motion signal based on at least the transaxial activity position versus time curve.

18. The emission imaging data processing device of claim 17, wherein the respiratory motion signal generation method further includes:

computing a transverse activity position versus time curve from the activity maps, the transverse activity position comprising a position of the centroid of the activity map along a transverse direction parallel with an axial anatomical axis (z) of the imaging subject;

wherein the respiratory motion signal is generated further based on the transverse activity position versus time curve.

* * * * *